(12) United States Patent
Kobayashi et al.

(10) Patent No.: US 9,725,337 B2
(45) Date of Patent: Aug. 8, 2017

(54) ULTRAVIOLET IRRADIATION APPARATUS

(71) Applicant: KABUSHIKI KAISHA TOSHIBA, Minato-ku, Tokyo (JP)

(72) Inventors: Shinji Kobayashi, Tokyo (JP); Norimitsu Abe, Kanagawa (JP); Takeshi Ide, Tokyo (JP); Akihiko Shirota, Tokyo (JP); Kenji Takeuchi, Tokyo (JP); Takahiro Soma, Tokyo (JP)

(73) Assignee: KABUSHIKI KAISHA TOSHIBA, Tokyo (JP)

(*) Notice: Subject to any disclaimer, the term of this patent is extended or adjusted under 35 U.S.C. 154(b) by 46 days.

(21) Appl. No.: 14/479,091

(22) Filed: Sep. 5, 2014

(65) Prior Publication Data

US 2014/0374613 A1 Dec. 25, 2014

Related U.S. Application Data

(63) Continuation of application No. PCT/JP2013/051775, filed on Jan. 28, 2013.

(30) Foreign Application Priority Data

Mar. 6, 2012 (JP) ................................. 2012-049741

(51) Int. Cl.
*C02F 1/32* (2006.01)
*A61L 2/10* (2006.01)
(Continued)

(52) U.S. Cl.
CPC ............... *C02F 1/325* (2013.01); *A61L 2/10* (2013.01); *A61L 2209/10* (2013.01);
(Continued)

(58) Field of Classification Search
CPC .................................... C02F 1/32; C02F 1/325
See application file for complete search history.

(56) References Cited

U.S. PATENT DOCUMENTS 3,683,177 A * 8/1972 Veloz .................... A61L 2/10
119/245
4,629,896 A * 12/1986 Bridgen .................. C02F 1/325
250/372
(Continued)

FOREIGN PATENT DOCUMENTS

| JP | 2001-343287 A | 12/2001 |
| JP | 2004-251754 A | 9/2004 |

(Continued)

OTHER PUBLICATIONS

International Preliminary Report on Patentability for application No. PCT/JP2013/051775, issued on Sep. 9, 2014, by Mineko Mohri.
(Continued)

*Primary Examiner* — Casey Bryant
(74) *Attorney, Agent, or Firm* — Knobbe, Martens, Olson & Bear LLP

(57) ABSTRACT

An ultraviolet irradiation apparatus according to an embodiment includes a reaction tank including an inlet port for introducing to-be-treated water, and a discharge port for discharging to-be-treated water after treatment, a first ultraviolet lamp, and an ultraviolet monitor including an ultraviolet sensor. The first ultraviolet lamp is accommodated in a first protection tube including both end portions fixed in the reaction tank. The ultraviolet monitor is accommodated in a second protection tube, the second protection tube is disposed in parallel to the first protection tube, and both end portions of the second protection tube are fixed in the reaction tank.

12 Claims, 10 Drawing Sheets

(51) Int. Cl.
 *C02F 1/28* (2006.01)
 *C02F 1/52* (2006.01)
 *C02F 1/76* (2006.01)

(52) U.S. Cl.
 CPC ............ *C02F 1/283* (2013.01); *C02F 1/52* (2013.01); *C02F 1/76* (2013.01); *C02F 2201/326* (2013.01); *C02F 2201/3227* (2013.01); *C02F 2303/02* (2013.01); *C02F 2303/04* (2013.01)

(56) References Cited

U.S. PATENT DOCUMENTS

| | | | | |
|---|---|---|---|---|
| 6,197,203 | B1 * | 3/2001 | Ishida | B01D 61/16 210/748.11 |
| 2002/0101574 | A1 | 8/2002 | Tsuji | |
| 2013/0068964 | A1 * | 3/2013 | Kobayashi | C02F 1/325 250/431 |
| 2016/0046507 | A1 * | 2/2016 | Deguchi | G01J 1/58 250/432 R |

FOREIGN PATENT DOCUMENTS

| | | |
|---|---|---|
| JP | 3881183 B2 | 11/2006 |
| JP | 2007-155546 A | 6/2007 |
| JP | 2007155546 A * | 6/2007 |
| JP | 4168348 B2 | 8/2008 |
| JP | 2011-050830 A | 3/2011 |
| WO | WO 99/39375 A1 | 8/1999 |

OTHER PUBLICATIONS

International Search Report and Written Opinion for application No. PCT/JP2013/051775, mailed on Apr. 16, 2013.

* cited by examiner

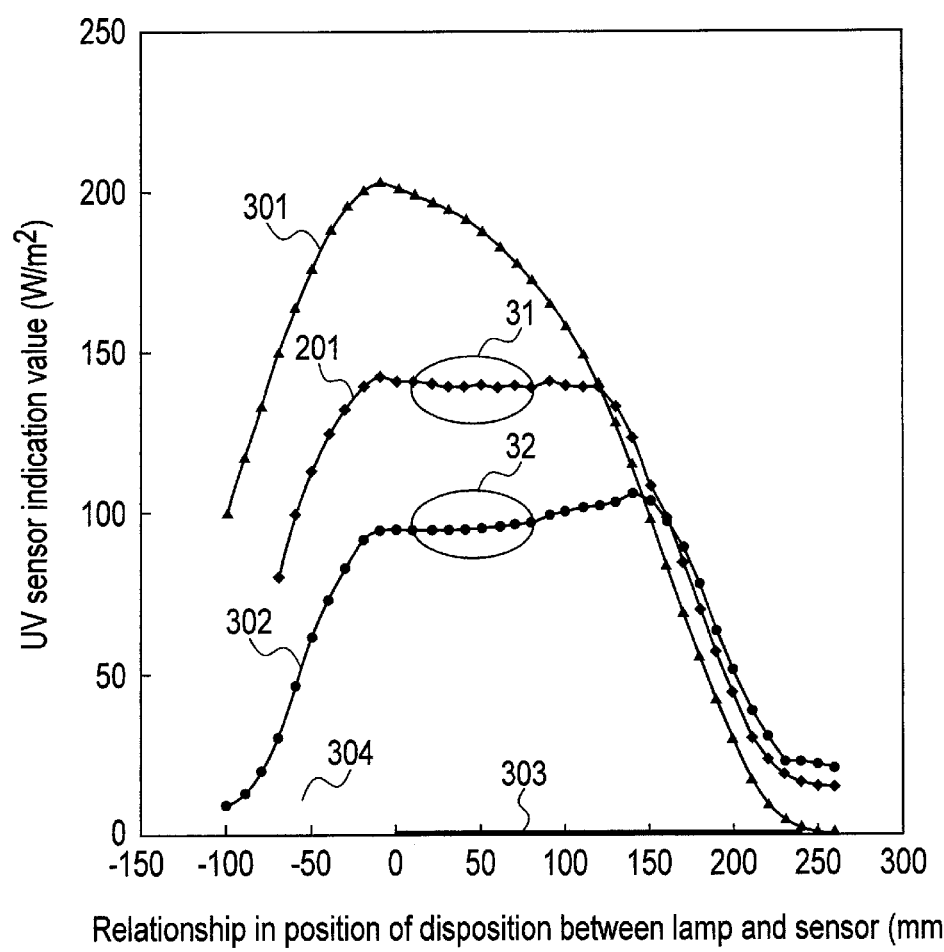
F I G. 14

ULTRAVIOLET IRRADIATION APPARATUS

CROSS-REFERENCE TO RELATED APPLICATIONS

This application is based upon and claims the benefit of priority from Japanese Patent Application No. 2012-049741, filed Mar. 6, 2012, International Patent Application No. PCT/JP2013/051775, filed Jan. 28, 2013, the entire contents of both of which are incorporated herein by reference.

FIELD

Embodiments described herein relate generally to an ultraviolet irradiation apparatus which performs sterilization and disinfection by making use of ultraviolet.

BACKGROUND

Chemicals, such as ozone and chlorine, are used to perform sterilization/disinfection of clean water and waste water, deodorization/decolorization of industrial water, bleaching of pulp, sterilization of medical equipment, etc.

In a conventional disinfection apparatus, a retention tank or a stirring device such as a spray pump is indispensable in order to uniformly dissolve ozone or chemical in treatment water, and it is not possible to immediately adapt to a change in water quality or water amount. Ultraviolet includes functions of, for example, sterilization, disinfection, decolorization, deodorization/decolorization of industrial water, bleaching of pulp, etc., and an ultraviolet process is performed in order to immediately adapt to a change in water quality or water amount.

However, in an ultraviolet irradiation apparatus which is capable of performing a large-scale process, since the amount of water is large, the diameter of a water conduit increases. Thus, there is danger that an ultraviolet monitoring window of an ultraviolet monitor, which monitors an ultraviolet lamp disposed in the middle of the water conduit, and equipment thereof, are vibrated and damaged by a water flow.

BRIEF DESCRIPTION OF DRAWINGS

FIG. 14 is a graph representing a relationship between a surface of a light reception part of the ultraviolet sensor and a position of the light shield plate.

DETAILED DESCRIPTION

In general, according to one embodiment, an ultraviolet irradiation apparatus includes a reaction tank, a first ultraviolet lamp, and an ultraviolet monitor. The reaction tank includes an inlet port for introducing to-be-treated water, and a discharge port for discharging to-be-treated water after treatment. The first ultraviolet lamp is accommodated in a first protection tube including at least both end portions fixed in the reaction tank, the first ultraviolet lamp being configured to subject the to-be-treated water to an ultraviolet irradiation process. The ultraviolet monitor is accommodated in a second protection tube which is disposed in parallel to the first protection tube and includes at least both end portions fixed to the reaction tank, the ultraviolet monitor including an ultraviolet sensor configured to detect ultraviolet from the first ultraviolet lamp, and the ultraviolet monitor being configured to monitor an irradiation amount of ultraviolet.

An ultraviolet irradiation apparatus according to an embodiment may be used in a clear water treatment system.

Figure 1:
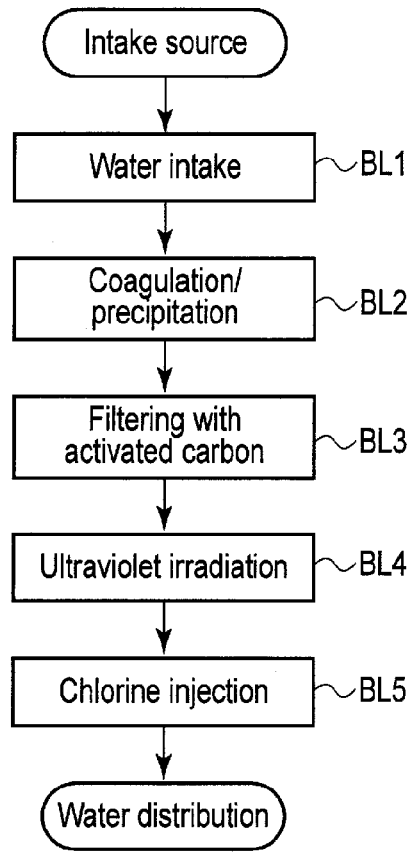
FIG. 1 is a flowchart illustrating a clean water treatment system of an embodiment.

FIG. 1 is a flowchart illustrating a clear water treatment system.

As illustrated in FIG. 1, in the clear water treatment system, for example, raw water is taken in from an intake source such as a river, a lake, or underground water (BL1). The obtained raw water is coagulated and precipitated (BL2). Treatment water is filtered with activated carbon (BL3). The filtered treatment water is subjected to an ultraviolet irradiation process through an ultraviolet irradiation apparatus, thereby being sterilized, disinfected and inactivated (BL4). Chlorine is injected in the obtained treatment water (BL5), and the resultant water is distributed to general houses, business offices, etc.

The ultraviolet irradiation apparatus according to the embodiment is an ultraviolet irradiation apparatus which may be used in BL4 in the above-described clear water system. The ultraviolet irradiation apparatus includes a reaction tank including an inlet port for introducing to-be-treated water, and a discharge port for discharging water after treatment; a first ultraviolet lamp configured to subject the to-be-treated water to an ultraviolet irradiation process; and an ultraviolet monitor including an ultraviolet sensor configured to detect ultraviolet radiated from the first ultraviolet lamp.

The first ultraviolet lamp is used in order to subject to-be-treated water to an ultraviolet irradiation process. The first ultraviolet lamp is accommodated in a first protection tube. At least both end portions of the first protection tube are fixed in the reaction tank.

The ultraviolet monitor is used in order to monitor an irradiation amount of ultraviolet from the ultraviolet lamp. The ultraviolet monitor is accommodated in a second protection tube. The second protection tube is disposed in parallel to the first protection tube, and at least both end portions of the second protection tube are fixed in the reaction tank.

According to the ultraviolet irradiation apparatus of the embodiment, since at least two points (both end portions) or three or more points of the protection tube, in which the ultraviolet monitor is accommodated, are fixed in the reaction tank, it is possible to prevent vibration breakage due to a water flow, etc.

In the ultraviolet irradiation apparatus according to the embodiment, a second ultraviolet lamp, which is accommodated in a third protection tube including at least both end portions fixed in the reaction tank, can further be provided. At this time, the second protection tube, in which the ultraviolet monitor is accommodated, may be disposed between, and in parallel to, the first and third protection tubes each accommodating the ultraviolet lamp.

According to the ultraviolet irradiation apparatus of the embodiment, since the protection tube, in which the ultraviolet lamp is accommodated, is disposed in parallel to the protection tube in which the ultraviolet monitor is accommodated, a single ultraviolet monitor can monitor, at the same time, ultraviolet lights of a plurality of ultraviolet lamps in the surrounding area of the ultraviolet monitor.

Figure 2:
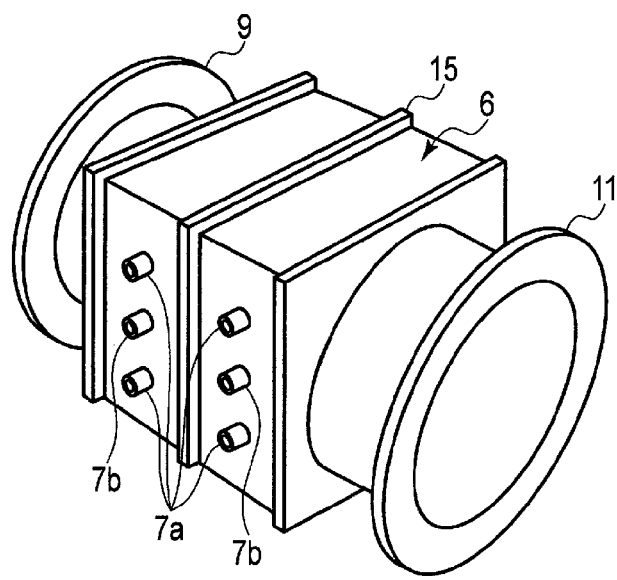
FIG. 2 is a view illustrating an external appearance of an example of an ultraviolet irradiation apparatus according to a first embodiment.

FIG. 2 is a view illustrating an external appearance of an ultraviolet irradiation apparatus according to a first embodiment.

As illustrated in FIG. 2, the ultraviolet irradiation apparatus according to the first embodiment includes a rectangular reaction tank 6; a water supply port 9 which is provided in one side surface of four side surfaces of the reaction tank 6 and in which treatment water flows; a discharge port 11 which is provided in a side surface opposed to the one side surface and which discharges the treatment water; and six protection tubes 7a and 7b which are horizontally provided and include their both end portions fixed to one and the other of the other two side surfaces. The end portions of the six protection tubes 7a and 7b are disposed in two rows in the horizontal direction and in three rows in the vertical direction, as viewed from one side surface. Each of the two sets of three vertical rows is arranged in the order of protection tubes 7a, 7b and 7a.

The protection tube 7a is formed of a dielectric body, such as quartz glass, which can pass ultraviolet, and an ultraviolet lamp 8 is accommodated in the protection tube 7a.

The protection tube 7b is formed of a dielectric body, such as quartz glass, which can pass ultraviolet, and an ultraviolet sensor 12 of an ultraviolet monitor for monitoring an irradiation amount of ultraviolet is disposed in the protection tube 7b.

In the meantime, examples of the material of the protection tube include quartz glass and Teflon (trademark).

As illustrated in FIG. 2, ribs 15 are disposed on the side surfaces and upper and lower surfaces of the rectangular reaction tank 6, thereby suppressing deformation of the entirety of the reaction tank due to an increase in internal pressure.

Figure 3:
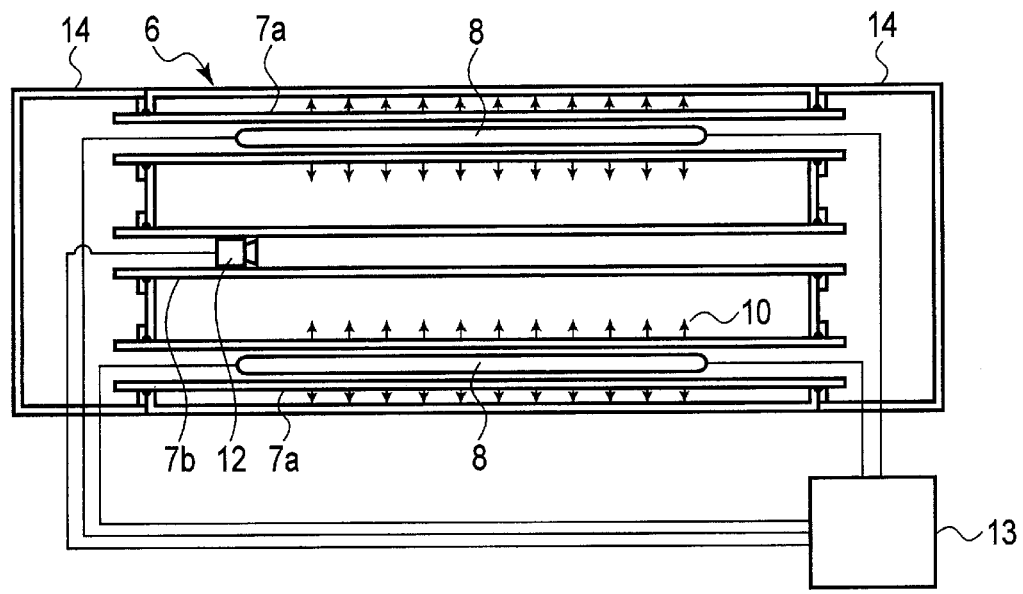
FIG. 3 is a view illustrating an example of a vertical cross section of FIG. 2.

FIG. 3 is a view illustrating an example of a vertical cross section of one set of three vertically arranged protection tubes 7a, 7b and 7a shown in FIG. 2.

Figure 4:
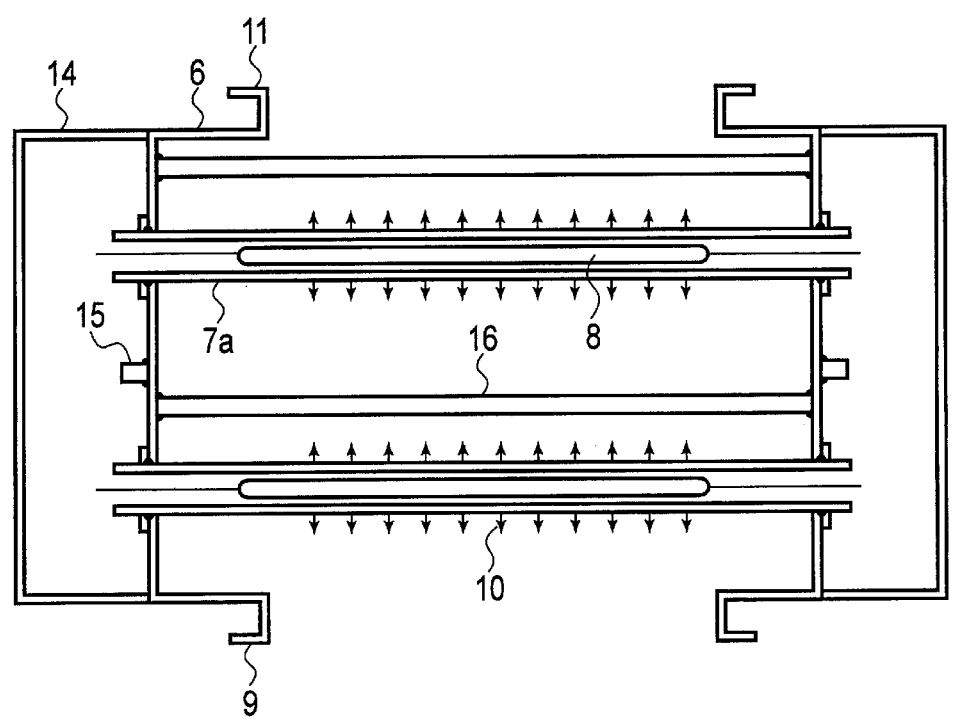
FIG. 4 is a view illustrating an example of a horizontal cross section of FIG. 2.

FIG. 4 is a view illustrating an example of a horizontal cross section of one set of two horizontally arranged protection tubes 7a, 7a shown in FIG. 2.

Figure 5:
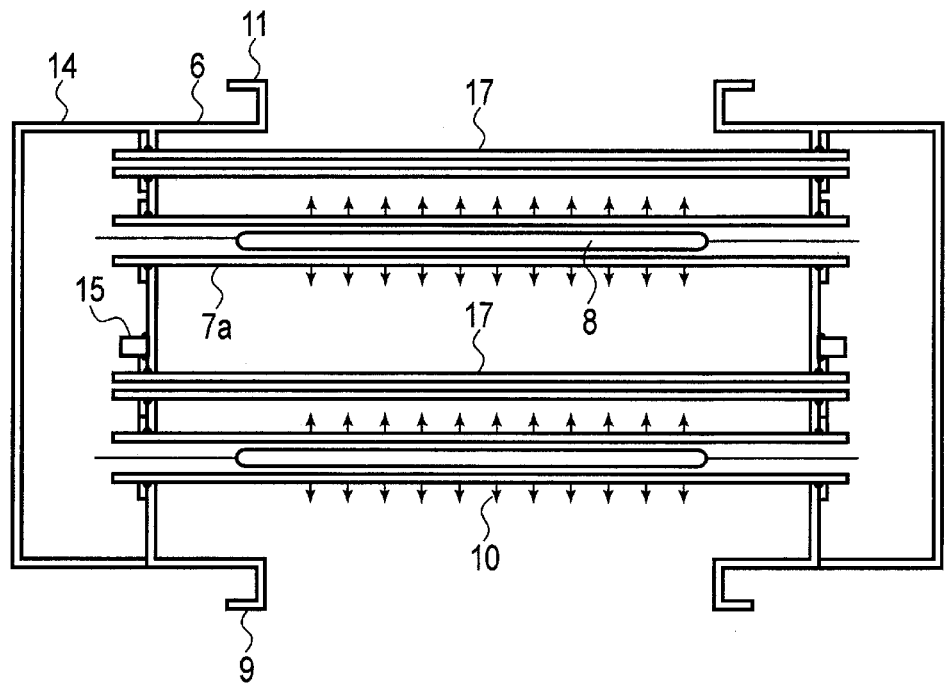
FIG. 5 is a view illustrating another example of the horizontal cross section of FIG. 2.

FIG. 5 is a view illustrating another example of the horizontal cross section of one set of two horizontally arranged protection tubes 7a, 7a shown in FIG. 2.

Treatment water flows in the reaction tank 6 from the water supply port 9. Bacteria included in the treatment water are sterilized, disinfected and inactivated by ultraviolet light 10 which is radiated from the ultraviolet lamps 8, and the resultant water flows out of the discharge port 11. Each ultraviolet lamp 8 is connected to an electronic ballast 13.

Although not shown in FIG. 2, protection covers 14, which shield ultraviolet as illustrated in FIG. 3, are attached to power supply parts at both end portions fixed to the reaction tank 6.

On the other hand, since the protection tubes 7a and 7b are formed of quartz glass, the resiliency of the protection tubes 7a and 7b is low. If the reaction tank deforms, the protection tubes 7a and 7b may easily be broken. Thus, in the reaction tank 6, as illustrated in FIG. 4 and FIG. 5, a support rod 16 or support pipes 17 for preventing deformation are disposed.

In the meantime, in the reaction tank 6 in which the support rod 16 or pipes 17 are disposed in parallel to the protection tubes 7a and 7b, the support rod 16 or pipes 17 are disposed behind the protection tubes 7a and 7b, thereby suppressing the influence upon the ultraviolet irradiation amount by a turbulent flow which occurs due to the support rod or pipes.

According to the ultraviolet irradiation apparatus of the embodiment, at least both end portions of the protection tube, which accommodates the ultraviolet monitor, are fixed in the reaction tank. Thus, vibration breakage due to a water flow can be prevented, and sterilization, disinfection and inactivation of to-be-treated water can be performed within several seconds. A single ultraviolet monitor can monitor, at the same time, ultraviolet lights of two ultraviolet lamps in the surrounding area of the single ultraviolet monitor. In addition, if the ultraviolet irradiation apparatus of the embodiment is used, the output of the ultraviolet lamps can be varied and the intensity of ultraviolet can be controlled in accordance with a measurement result of the irradiation amount of ultraviolet, and the power that is consumed can be suppressed.

In order to prevent vibration breakage due to a swirl caused by a water flow, both end portions of the protection tubes 7a and 7b may not only be fixed in the reaction tank, but the protection tubes 7a and 7b may also be chosen with a diameter and a thickness which satisfy the following equation (1):

$$\text{equivalent flow velocity (reference) } Vr=U/(fn \times Do)<1 \quad (1)$$

where
reference flow velocity $U=Qmax/Sd$
characteristic frequency $fn=(\lambda^2)(2\pi L^2) \times (EI/(m+mw))^{1/2}$
characteristic value $\lambda=3.1415$
geometrical moment of inertia $I=\pi/64(Do^4)$
mass per unit $m=S\rho s$
excluded mass per unit $mw=Sw\rho w$
cross-sectional area of cylindrical part $S=\pi(Do/2)^2-(Din/2)^2$
inside diameter of protection tube $Din=Do-2t$
excluded area $Sw=\pi(Do/2)^2$, wherein in the equations, Do is an outside diameter of the protection tube, Qmax is a maximum flow rate, Sd is a cross-sectional area of a flow path, E is a Young's modulus of material of the protection tube, L is a length of the protection tube, t is a thickness of the protection tube, $\rho s$ is a density of material (e.g. quartz glass) of the protection tube, and ρw is a water density.

Examples of calculation values of the left side of equation (1) are shown below, in a case where a flow path pipe diameter d has been varied in the reaction tank of the ultraviolet irradiation apparatus shown in FIG. 2 to FIG. 4.

Example 1

The case in which the flow path pipe diameter d is 0.8 m.

| | |
|---|---|
| outside diameter Do of protection tube | 0.036 m |
| thickness t of protection tube | 0.003 m |
| inside diameter of protection tube Din = Do − 2t | 0.03 m |
| length L of protection tube | 1 m |
| material synthetic quartz glass | |
| Young's modulus E of protection tube material | 70,000 N/mm²[MPa] |
| density ρs of protection tube material (e.g. quartz glass) | 2201 kg/m³ |
| cross-sectional area of cylindrical part $S = \pi(Do/2)^2 - (Din/2)^2$ | 0.000311018 m² |
| mass per unit m = Sρs | 0.684549898 kg/m |
| geometrical moment of inertia $I = \pi/64(Do^4)$ | 4.26872 × 10⁸ m⁴ |
| water density ρw (condition: 290 K, 0.1 MPa) | 996.66 kg/m³ |
| excluded area $Sw = \pi(Do/2)^2$ | 0.001017876 m² |
| excluded mass per unit mw = Swρw | 1.014476314 kg/m |
| characteristic value λ = 3.1415 | |
| characteristic frequency $fn = (\lambda^2)(2\pi L^2) \times (EI/(m + mw))^{1/2}$ | 65.87453578 Hz |
| reference flow rate Q | 0.578703704 m²/s |
| maximum flow rate Qmax | 0.868055556 m³/s |
| flow path pipe diameter d | 0.8 m |
| cross-sectional area of flow path Sd | 0.502654825 m² |
| mean reference flow velocity U = Qmax/Sd | 1.151294438 m/s |
| mean maximum flow velocity U | 1.726941657 m/s |
| equivalent flow velocity (reference) Vr = U/(fn × Do) | 0.485474405 |
| equivalent flow velocity (maximum) | 0.728211607 |
| protection tube width in flow path | 0.8 m |
| minimum flow path cross-sectional area Sd | 0.473854825 m² |
| mean reference flow velocity Umax | 1.221267936 m/s |
| mean maximum flow velocity Umax | 1.831901904 m/s |
| equivalent flow velocity (reference) Vr = U/(fn × Do) | 0.514980621 |
| equivalent flow velocity (maximum) | 0.772470931. |

The thus obtained equivalent flow velocity Vr in the case of the reference flow rate Q, i.e. Vr=U/(fn×Do)=0.485474405, is less than 1, and the equivalent flow rate at the time of maximum flow rate Qmax, i.e. Vr=U/(fn×Do)=0.514980621, is less than 1. It is thus understood that Example 1 satisfies equation (1).

Comparative Example 1

| | |
|---|---|
| outside diameter Do of protection tube | 0.036 m |
| thickness t of protection tube | 0.003 m |
| inside diameter of protection tube Din = Do − 2t | 0.03 m |
| length L of protection tube | 1 m |
| material synthetic quartz glass | |
| Young's modulus E of protection tube material | 70,000 N/mm²[MPa] |
| density ρs of protection tube material (e.g. quartz glass) | 2201 kg/m³ |
| cross-sectional area of cylindrical part $S = \pi(Do/2)^2 - (Din/2)^2$ | 0.000311018 m² |
| mass per unit m = Sρs | 0.684549898 kg/m |
| geometrical moment of inertia $I = \pi/64(Do^4)$ | 4.26872 × 10⁸ m⁴ |
| water density ρw (condition: 290 K, 0.1 MPa) | 996.66 kg/m³ |
| excluded area $Sw = \pi(Do/2)^2$ | 0.001017876 m² |
| excluded mass per unit mw = Swρw | 1.014476314 kg/m |
| characteristic value λ = 3.1415 | |
| characteristic frequency $fn = (\lambda^2)(2\pi L^2) \times (EI/(m + mw))^{1/2}$ | 65.87453578 Hz |
| reference flow rate Q | 0.578703704 m²/s |
| maximum flow rate Qmax | 0.868055556 m³/s |
| flow path pipe diameter d | 0.45 m |
| cross-sectional area of flow path Sd | 0.159043128 m² |
| mean reference flow velocity U = Qmax/Sd | 3.638658964 m/s |
| mean maximum flow velocity U | 5.457988446 m/s |
| equivalent flow velocity (reference) Vr = U/(fn × Do) | 1.53433886 |
| equivalent flow velocity (maximum) Vr | 2.301508289 |
| protection tube width in flow path | 0.45 m |
| minimum flow path cross-sectional area Sd | 0.142843128 m² |
| mean reference flow velocity Umax | 4.051323374 m/s |
| mean maximum flow velocity Umax | 6.076985062 m/s |
| equivalent flow velocity (reference) Vr = U/(fn × Do) | 1.708349957 |
| equivalent flow velocity (maximum) | 2.562524936. |

The thus obtained equivalent flow velocity (reference) Vr at the time of the reference flow velocity, i.e. Vr=U/(fn×Do)=1.53433886, is greater than 1, and the equivalent flow velocity Vr at the time of maximum flow rate Qmax, i.e. Vr=U/(fn×Do)=1.708349957, is greater than 1. Thus, since Example 1 fails to satisfy equation (1), it is understood that vibration breakage due to a water flow, etc. tends to easily occur.

As illustrated in FIG. 3, the axis of the view field of the ultraviolet sensor 12 of the ultraviolet monitor, which is disposed in the protection tube, can be disposed in parallel to the axes of the ultraviolet lamps 8 which are to be monitored.

Figure 6:
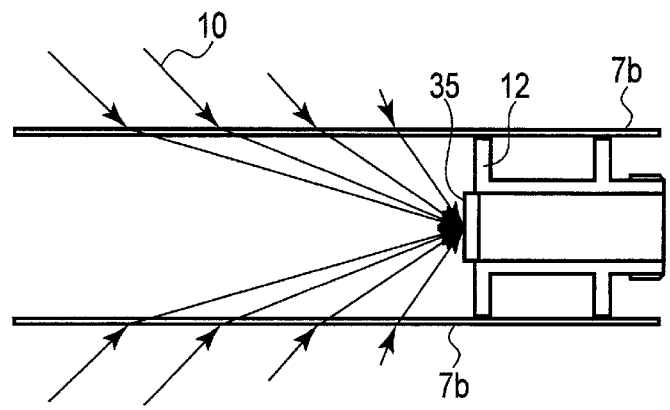
FIG. 6 is a view illustrating an example of trajectories of light paths of ultraviolet light which is radiated on an ultraviolet sensor.

FIG. 6 illustrates an example of trajectories of light paths of ultraviolet lights which are radiated from the ultraviolet lamps to the ultraviolet sensor.

When the axis of the view field of the ultraviolet sensor 12 of the ultraviolet monitor, which is disposed in the protection tube, is disposed in parallel to the axes of the ultraviolet lamps, those ultraviolet light components 10, among the ultraviolet lights from the ultraviolet lamps 8, which are radiated from an obliquely forward direction of the view field of the ultraviolet sensor 12, can be monitored.

Figure 7:
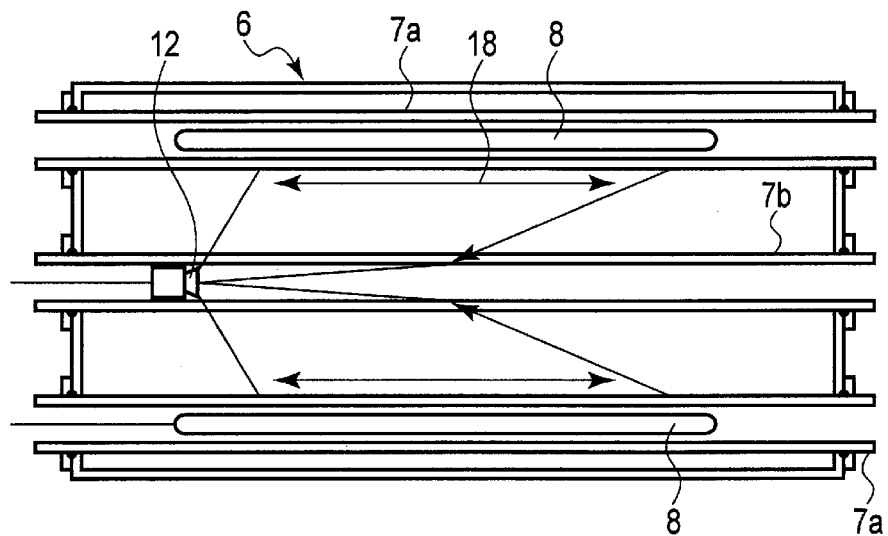
FIG. 7 is a view illustrating a monitoring view field in the ultraviolet irradiation apparatus according to the embodiment.

FIG. 7 is a view illustrating a monitoring view field in the ultraviolet irradiation apparatus.

As illustrated in FIG. 7, a monitoring view field 18 in the ultraviolet irradiation apparatus ranges over an area extending in an obliquely forward direction of the ultraviolet sensor 12, and it is possible to monitor ultraviolet lights from a plurality of ultraviolet lamps 8 which are disposed in parallel to, and in the surrounding area of, the protection tube 7b which accommodates the ultraviolet monitor.

Figure 8:
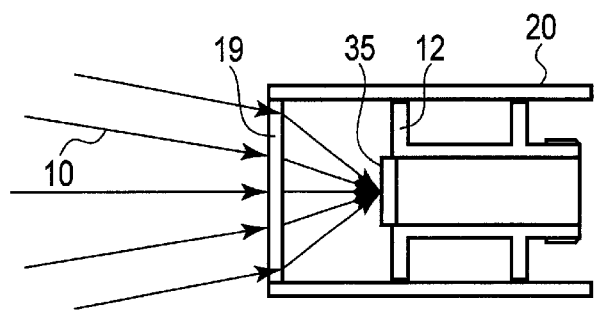
FIG. 8 is a schematic cross-sectional view illustrating an example of an ultraviolet monitor which is used in the embodiment.

FIG. 8 is a schematic cross-sectional view illustrating an example of an ultraviolet monitor which is used in the embodiment.

As shown in FIG. 8, the ultraviolet monitor includes an ultraviolet sensor 12, and an ultraviolet non-transmissive light shield cylinder 20 including an ultraviolet monitoring window 19 on a light reception part side of the ultraviolet sensor 12. Ultraviolet light 10 enters the ultraviolet sensor 12 through the ultraviolet monitoring window 19. Thus, if this ultraviolet monitor is used, ultraviolet light 10 from a far side of the ultraviolet monitoring window 19 is measured.

In the protection tube in which the ultraviolet monitor is accommodated, when the axis of the view field of the ultraviolet monitor is disposed in parallel to the axis of the lamp, the view field is wide and ultraviolet light, which is refracted at interfaces of "water/protection tube glass/air", is incident. Thus, there is a tendency that the actual measurement precision of the ultraviolet monitor depends greatly on the precision in position of disposition. Meanwhile, a component, which restricts the view field, can be attached to the ultraviolet sensor of the ultraviolet monitor that is disposed in the protection tube. Thereby, it becomes possible to select an ultraviolet lamp which is a target of monitoring, and to monitor a specific part of the ultraviolet lamp.

Figure 9:
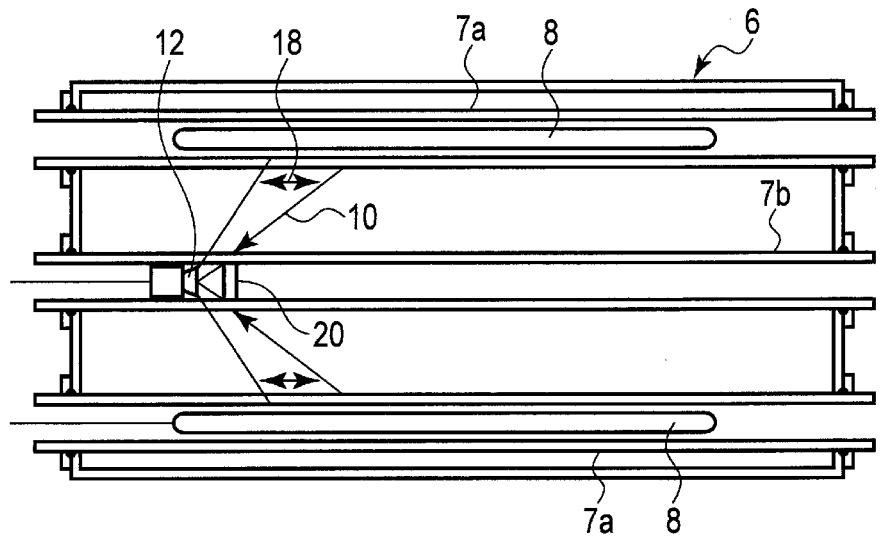
FIG. 9 is a view illustrating a monitoring view field in an ultraviolet irradiation apparatus in which a light shield plate is disposed.

FIG. 9 is a view illustrating a monitoring view field in an ultraviolet irradiation apparatus in which a light shield plate is disposed as a component which restricts the view field.

The monitoring view field 18 in the ultraviolet irradiation apparatus is a partial area in an obliquely forward direction of the ultraviolet sensor 12, and ultraviolet light 10 in this area from plural ultraviolet lamps, which are disposed in parallel to, and in the surrounding area, of the protection tube 7b which accommodates the ultraviolet monitor, can be monitored.

Figure 10:
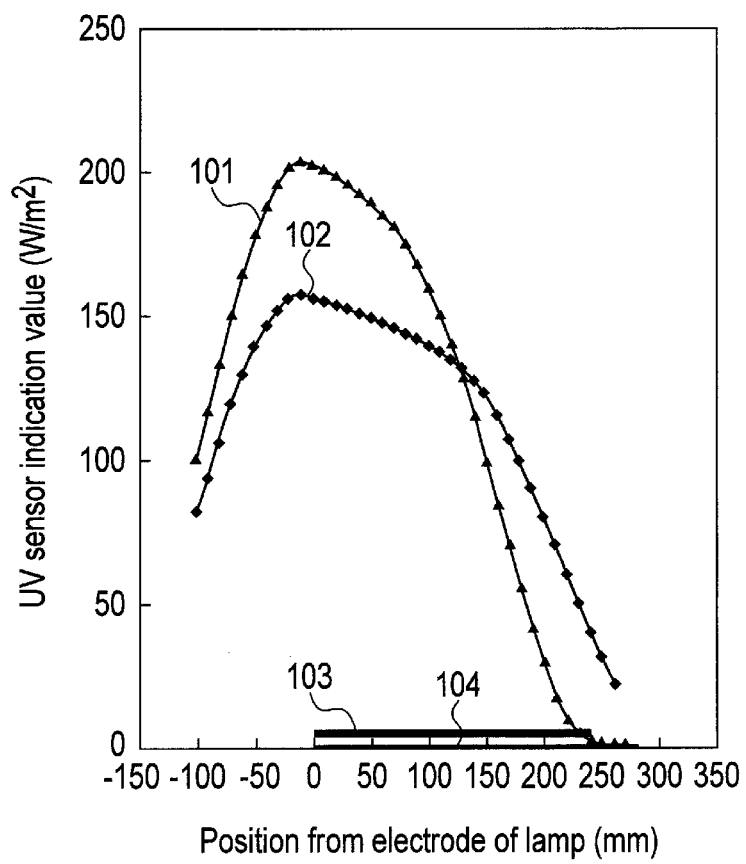
FIG. 10 is a graph representing a relationship between positions of an ultraviolet lamp and an ultraviolet sensor and an output of an ultraviolet monitor in a case where a light shield plate is not provided.

FIG. 10 is a graph representing a relationship between positions of an ultraviolet lamp and an ultraviolet sensor and an output of an ultraviolet monitor in a case where a light shield plate is not provided.

In FIG. 10, a graph 101 represents a relationship between an indication value ($W/m^2$) of the ultraviolet sensor which is not equipped with a light shield plate, and a position from the electrode of an ultraviolet lamp, in a case where the ultraviolet lamp with an emission length of 239 mm was used with an input of 3 kW. A graph 102 represents a relationship between an indication value ($W/m^2$) of the ultraviolet sensor which is not equipped with a light shield plate, and a position from the electrode of an ultraviolet lamp, in a case where the ultraviolet lamp with an emission length of 289 mm was used with an input of 3 kW. A graph 103 indicates an emission position (0 to 239 mm) of the ultraviolet lamp, and a graph 104 indicates an emission position (0 to 289 mm) of the ultraviolet lamp.

As shown in FIG. 10, the indication value of the ultraviolet sensor without a light shield plate varies in accordance with the position in the axial direction of the ultraviolet lamp and ultraviolet sensor. When the sensor is disposed just beside the electrode, the indication value takes a maximum value, and there is no region where a fixed value is indicated. In addition, if the length of the light emission tube of the ultraviolet lamp varies, the coordinate positions are extended, but the indication value of the ultraviolet sensor is not indicative of a fixed value.

Figure 11:
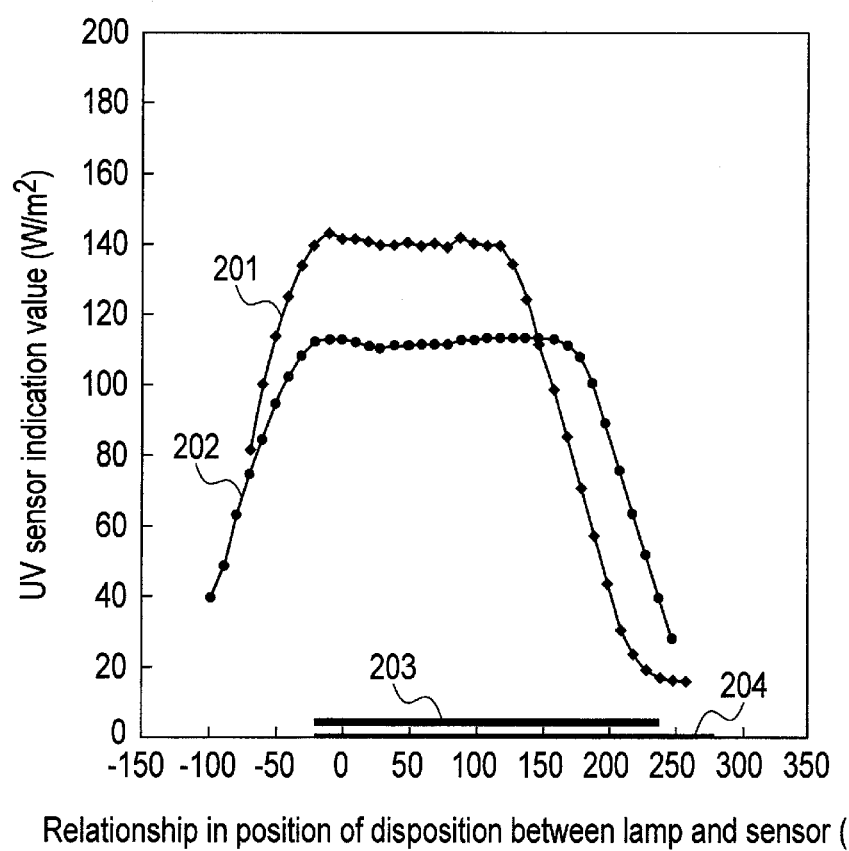
FIG. 11 is a graph representing a relationship between a position of an ultraviolet sensor, relative to an ultraviolet lamp, and an output of an ultraviolet monitor in a case where a light shield plate is provided.

FIG. 11 is a graph representing a relationship between a position of an ultraviolet sensor, relative to an ultraviolet lamp, and an output of an ultraviolet monitor in a case where a light shield plate is provided.

In FIG. 11, a graph 201 represents a relationship between an indication value ($W/m^2$) of the ultraviolet sensor which is equipped with a light shield plate, and a position from the electrode of an ultraviolet lamp, in a case where the ultraviolet lamp with an emission length of 239 mm was used with an input of 3 kW. A graph 202 represents a relationship between an indication value ($W/m^2$) of the ultraviolet sensor which is equipped with a light shield plate, and a position from the electrode of an ultraviolet lamp, in a case where the ultraviolet lamp with an emission length of 289 mm was used with an input of 3 kW. In each graph, the distance between the light shield plate and the light reception part 35 of the ultraviolet sensor is 20 mm. A graph 203 indicates an emission position (0 to 239 mm) of the ultraviolet lamp, and a graph 204 indicates an emission position (0 to 289 mm) of the ultraviolet lamp.

As shown in FIG. 11, except for a region just beside the electrode, the indication value of the ultraviolet sensor is not easily affected by the positional relationship in the axial direction between the ultraviolet lamp and ultraviolet sensor, and there is a region where a fixed value is indicated. If the length of the light emission tube of the ultraviolet lamp increases, the coordinate positions are extended depending on the positional relationship in the axial direction between the ultraviolet lamp and ultraviolet sensor.

Figure 12:
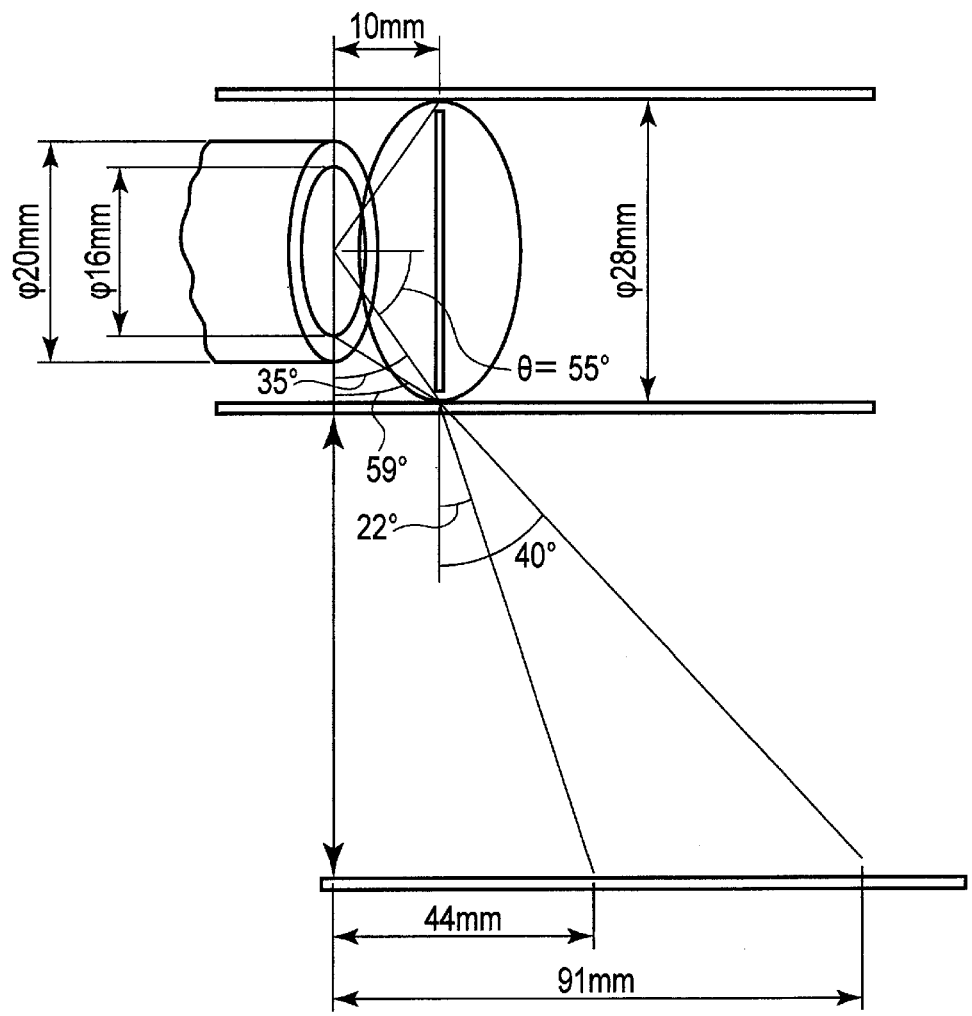
FIG. 12 is a view illustrating an example of a measuring view field at a time when a light shield plate is disposed.

FIG. 12 is a view illustrating an example of a measuring view field at a time when a light shield plate is disposed.

As illustrated in FIG. 12, for example, a light shield plate with a diameter of 28 mm is disposed at a distance of 10 mm from the surface of the light reception part 35 of the ultraviolet sensor 12 which is accommodated in a guide including an outside diameter of 20 mm, an inside diameter of 16 mm and a thickness of 2 mm. At this time, an angle θ of restriction of view field by the light shield plate is in a range of 0 to 55°, and the effective view field of the UV sensor is in a range of 35° between 55° to 90°. On the other hand, taking into account the refractive index of ultraviolet light at the interface of "water/quartz glass" and at the interface of "quartz glass/air", the effective view field is a range of 22° to 40° shown in FIG. 12. When the distance between the lamp and the sensor is 109 mm, the range of 47 mm between 91 mm and 44 mm in FIG. 12 becomes the range of monitoring of the effective view field.

Figure 13:
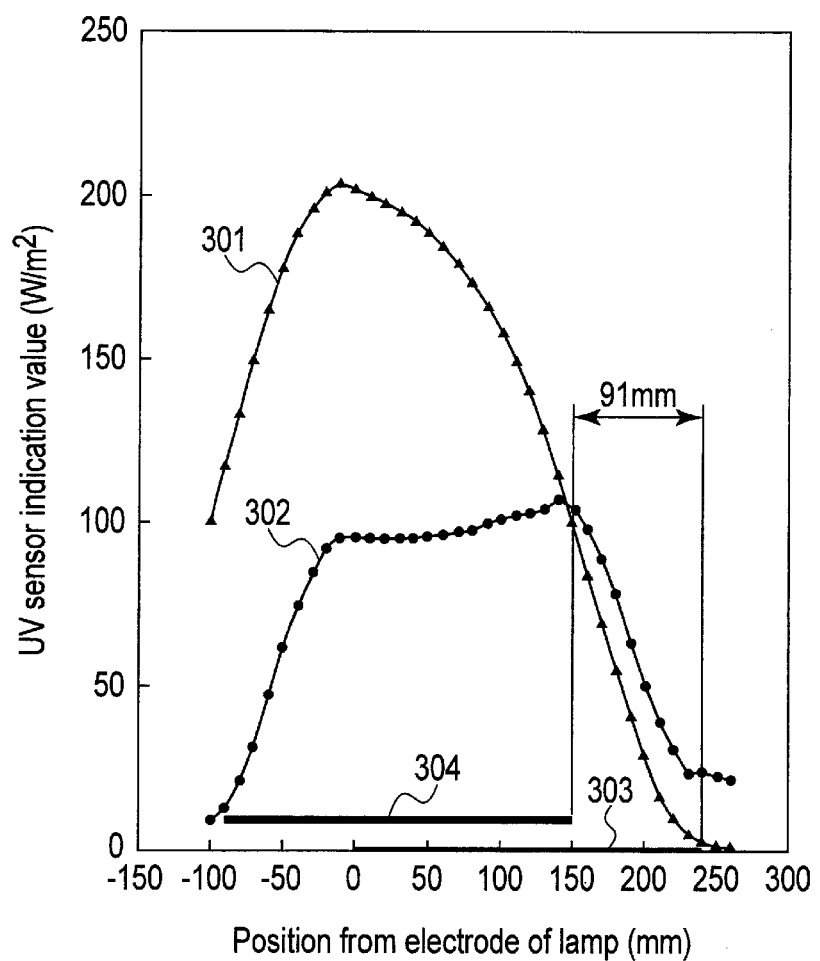
FIG. 13 is a graph representing a relationship between an indication value of the ultraviolet sensor and a position from an electrode of the ultraviolet lamp.

FIG. 13 represents a relationship between an indication value ($W/m^2$) of the ultraviolet sensor and a position (mm) from the electrode of the ultraviolet lamp in the case of FIG. 12.

In FIG. 13, a graph 301 represents a relationship between an indication value ($W/m^2$) of the ultraviolet sensor which is not equipped with a light shield plate, and a position (mm) from the electrode of the ultraviolet lamp, in the case of FIG. 12. A graph 302 represents a relationship between an indication value ($W/m^2$) of the ultraviolet sensor which is equipped with a light shield plate with a distance of 10 mm, and a position (mm) from the electrode of the ultraviolet lamp, in the case of FIG. 12. A graph 303 indicates a position (0 to 239 mm) of the ultraviolet lamp, and a graph 304 indicates a view field of the ultraviolet lamp, relative to the ultraviolet lamp.

FIG. 14 is a graph representing a relationship between a surface of a light reception part of the ultraviolet sensor and a position of the light shield plate.

A graph 301, as shown in FIG. 13, represents a relationship between an indication value ($W/m^2$) of the ultraviolet sensor which is not equipped with a light shield plate, and a position (mm) from the electrode of the ultraviolet lamp, in the case of FIG. 12. A graph 201, as shown in FIG. 11, represents a relationship between an indication value ($W/m^2$) of the ultraviolet sensor which is equipped with a light shield plate at a distance of 20 mm from the surface of the light reception part 35 of the ultraviolet sensor, and a position from the electrode of the ultraviolet lamp. A graph 302 represents a relationship between an indication value ($W/m^2$) of the ultraviolet sensor which is equipped with a light shield plate with a distance of 10 mm, and a position (mm) from the electrode of the ultraviolet lamp, in the case of FIG. 12. In each case, the ultraviolet lamp with an emission length of 239 mm was used with a lamp input of 3 kW.

As illustrated in FIG. 13 and FIG. 14, when the light shield plate is not provided, all ultraviolet light in the axial direction is detected. Thus, when the ultraviolet sensor is disposed just beside the electrode of the ultraviolet lamp, the indication value takes a maximum value. On the other hand, when the view field is restricted by the light shield plate, only the specific partial width of the ultraviolet lamp is monitored, and therefore the actual measurement precision of the ultraviolet monitor is not affected by the precision in position of disposition.

In addition, if the distance between the surface of the light reception part of the ultraviolet sensor and the light shield plate is varied, the indication value of the ultraviolet sensor varies. However, the indication value is not easily affected by the positional relationship in the axial direction between the ultraviolet lamp and the ultraviolet sensor, and there are regions 31 and 32 where fixed values are indicated. If the distal end of the ultraviolet sensor is disposed at the position of the region 31, 32, it becomes possible to monitor ultraviolet light, without being affected by the precision in position of disposition.

Figure 15:
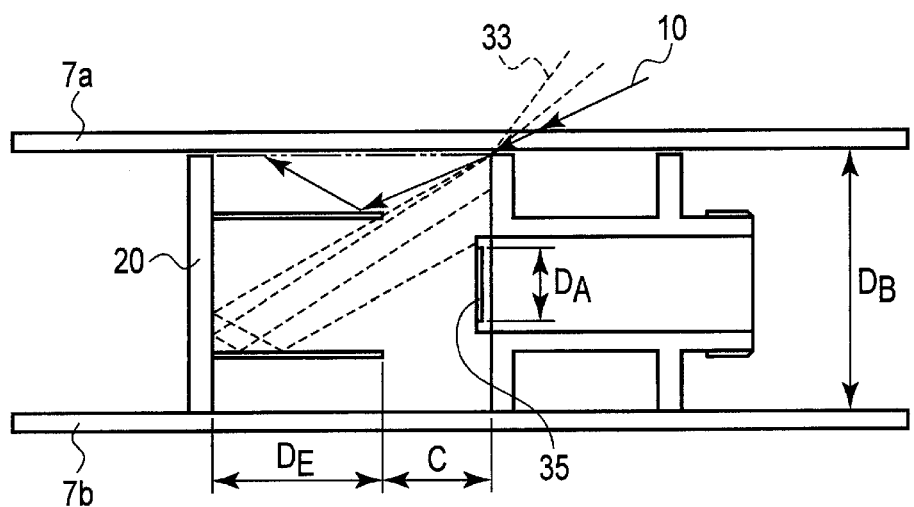
FIG. 15 is a view illustrating a monitoring view field in an ultraviolet irradiation apparatus according to another embodiment.

FIG. 15 is a view illustrating a monitoring view field in an ultraviolet irradiation apparatus in which another light shield part is disposed as the component which restricts the view field.

As illustrated in FIG. 15, instead of the light shield plate shown in FIG. 9, a cylindrical light shield part as shown in FIG. 15 can be disposed as the component that restricts the view field, with a fixed distance from the surface of the light reception part 35 of the ultraviolet sensor. If this cylindrical light shield part 21 is disposed, the ultraviolet light 10 from the back side of the ultraviolet sensor includes a trajectory as indicated by a broken line 33, and reflective light of ultraviolet, which is out of the target view field, is prevented from entering the ultraviolet sensor 12. In this example, the inside diameter DA of the light reception part 35 is set at 30 mm, the inside diameter DB of the protection tube is set at 30 mm, and the depth DE of the cylinder is set at 25 to 30 mm.

Aside from providing the component that restricts the view field, the inner surface or outer surface of the protection tube may be covered with, for example, a metal plating of aluminum, nickel, etc., coating, thermal spraying, etc. for shielding, thereby restricting the view field of the ultraviolet monitor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultraviolet irradiation apparatus comprising:
a reaction tank including an inlet port for introducing to-be-treated water, and a discharge port for discharging to-be-treated water after treatment;
a first ultraviolet lamp accommodated in a first protection tube including at least both end portions fixed in the reaction tank, the first ultraviolet lamp being configured to subject the to-be-treated water to an ultraviolet irradiation process; and
an ultraviolet monitor accommodated in a second protection tube which is disposed in parallel to the first protection tube and includes at least both end portions fixed to the reaction tank, the ultraviolet monitor including an ultraviolet sensor and a light shield plate, the ultraviolet sensor including a light reception part in a front surface of the ultraviolet sensor, the light reception part being configured to detect ultraviolet from the first ultraviolet lamp, the light shield plate being configured to restrict a view field of the ultraviolet sensor and being opposed to the front surface of the ultraviolet sensor in the second protection tube, and the ultraviolet monitor being configured to monitor an irradiation amount of ultraviolet.

2. The ultraviolet irradiation apparatus of claim 1, wherein the second protection tube includes ultraviolet transmissivity.

3. The ultraviolet irradiation apparatus of claim 2, wherein a surface of the second protection tube is covered with an ultraviolet non-transmissive material.

4. The ultraviolet irradiation apparatus of claim 1, wherein the second protection tube includes a diameter and a thickness which satisfy the following equation (1):

$$\text{equivalent flow velocity (reference) } Vr = U/(fn \times Do) < 1 \qquad (1)$$

where
mean reference flow velocity $U = Qmax/Sd$
characteristic frequency $fn = (\lambda^2)(2\pi L^2) \times (EI/(m+mw))^{1/2}$
characteristic value $\lambda = 3.1415$
geometrical moment of inertia $I = \pi/64(Do^4)$
mass per unit $m = S\rho s$
excluded mass per unit $mw = Sw\rho w$
cross-sectional area of cylindrical part $S = \pi(Do/2)^2 - (Din/2)^2$
inside diameter of protection tube $Din = Do - 2t$
excluded area $Sw = \pi(Do/2)^2$,
wherein in the equations, Do is an outside diameter of the protection tube, Qmax is a maximum flow velocity, Sd is a cross-sectional area of a flow path, E is a Young's modulus of material of the protection tube, L is a length of the protection tube, t is a thickness of the protection tube, $\rho s$ is a density of material of the protection tube, and $\rho w$ is a water density.

5. The ultraviolet irradiation apparatus of claim 4, wherein a surface of the second protection tube is covered with an ultraviolet non-transmissive material.

6. The ultraviolet irradiation apparatus of claim 1, wherein an axis of the view field of the ultraviolet sensor is parallel to an axis of the ultraviolet lamp.

7. The ultraviolet irradiation apparatus of claim 6, wherein a surface of the second protection tube is covered with an ultraviolet non-transmissive material.

8. The ultraviolet irradiation apparatus of claim 1, further comprising a second ultraviolet lamp accommodated in a third protection tube including at least both end portions fixed in the reaction tank, the second ultraviolet lamp being configured to subject the to-be-treated water to an ultraviolet irradiation process, the second protection tube being disposed between, and in parallel with, the first protection tube and the third protection tube.

9. The ultraviolet irradiation apparatus of claim 8, wherein a surface of the second protection tube is covered with an ultraviolet non-transmissive material.

10. The ultraviolet irradiation apparatus of claim 1, wherein the light shield plate includes a cylindrical reflection preventing member on a surface opposed to a front surface of the ultraviolet sensor.

11. The ultraviolet irradiation apparatus of claim 10, wherein a surface of the second protection tube is covered with an ultraviolet non-transmissive material.

12. The ultraviolet irradiation apparatus of claim 1, wherein a surface of the second protection tube is covered with an ultraviolet non-transmissive material.

* * * * *